United States Patent [19]
Kalin

[11] Patent Number: 5,647,849
[45] Date of Patent: Jul. 15, 1997

[54] SELF-CONTAINED SAFETY SYRINGE

[75] Inventor: Gerald James Kalin, Califon, N.J.

[73] Assignee: Becton, Dickinson and Company, Franklin Lakes, N.J.

[21] Appl. No.: 534,752

[22] Filed: Sep. 27, 1995

[51] Int. Cl.$^6$ ........................................... A61M 5/00
[52] U.S. Cl. ........................................ 604/111; 604/198
[58] Field of Search ........................... 604/111, 110, 604/192, 198, 263, 187

[56] References Cited

U.S. PATENT DOCUMENTS

| | | | |
|---|---|---|---|
| 4,929,232 | 5/1990 | Sweeney et al. | 604/111 |
| 5,188,613 | 2/1993 | Shaw | 604/111 X |
| 5,205,827 | 4/1993 | Novacek et al. | 604/111 X |
| 5,304,149 | 4/1994 | Morigi | 604/198 X |
| 5,312,370 | 5/1994 | Talonn et al. | 604/198 |

*Primary Examiner*—John D. Yasko
*Attorney, Agent, or Firm*—John L. Voellmicke

[57] ABSTRACT

A self-contained syringe includes a syringe barrel with a fluid receiving chamber. A plunger is slidably disposed in the chamber. A needle cannula is affixed to the distal end of the syringe barrel. A cap is releasably secured over proximal portions of both the plunger and the syringe barrel. A tubular shield is releasably engaged in an intermediate position on the syringe barrel such that distal portions of the shield surround the needle cannula. A removable or frangible sterile seal is secured over the extreme distal end of the shield. The cap and the seal may be removed immediately prior to use. The shield may then be moved proximally into a proximal position which exposes the needle cannula for use. The shield may then be moved distally and locked into distal position where the needle cannula is protectively surrounded.

16 Claims, 3 Drawing Sheets

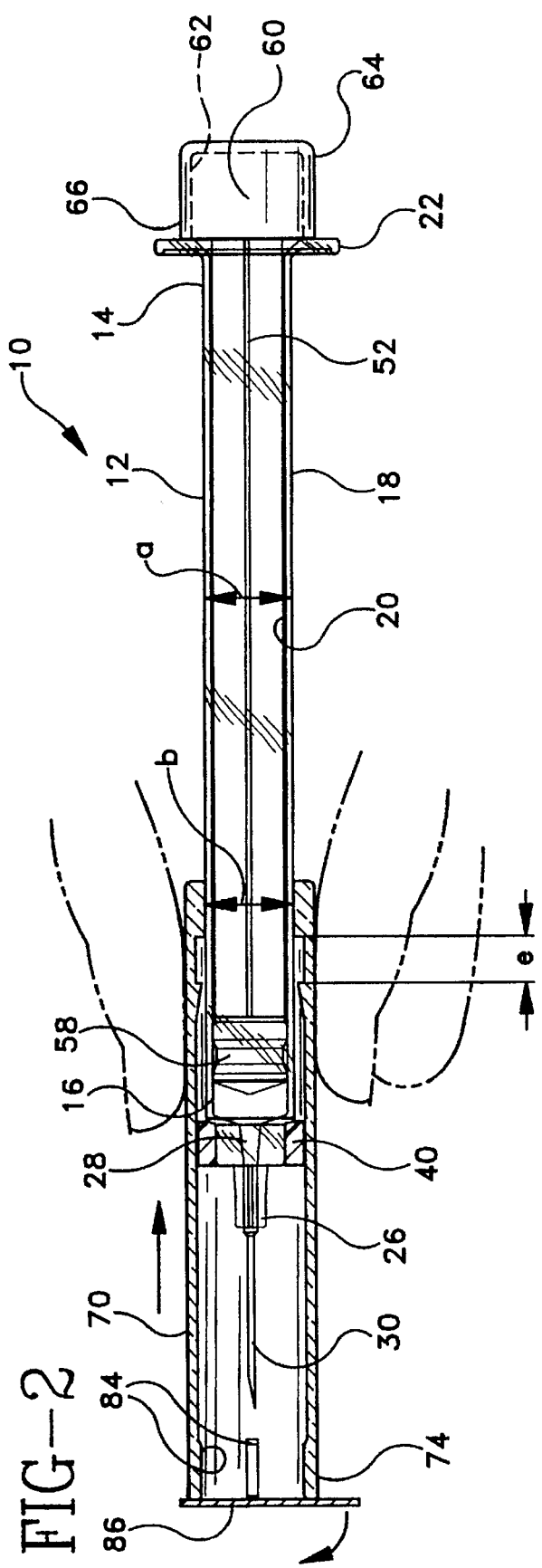
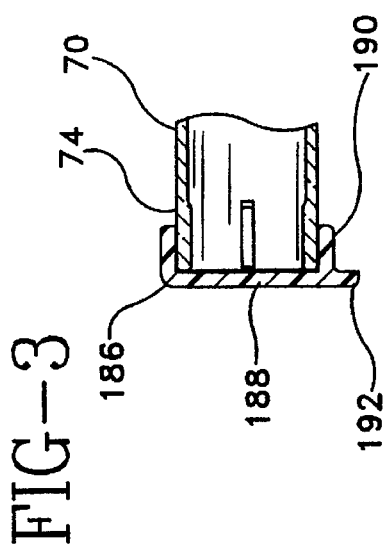
FIG-2
FIG-3

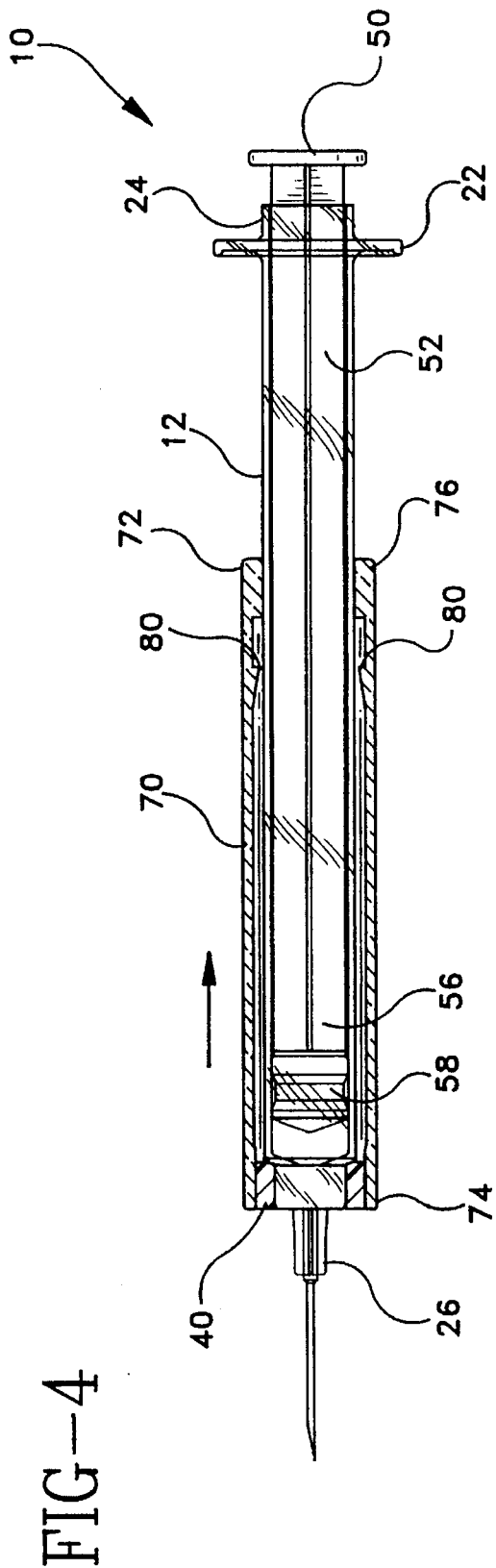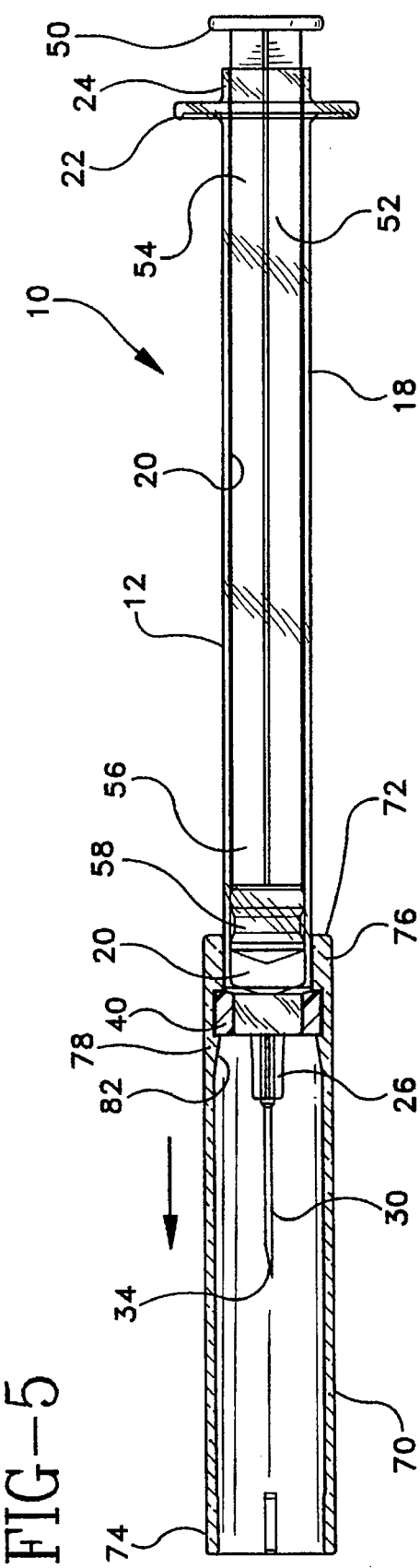

SELF-CONTAINED SAFETY SYRINGE

BACKGROUND OF THE INVENTION

1. Field of the Invention

The subject invention relates to a self-contained syringe with features for providing sterility, tamper evidence and needle shielding.

2. Background of the Invention

The prior art hypodermic syringe includes a generally cylindrical syringe barrel with opposed proximal and distal ends and a fluid receiving chamber therebetween. The proximal end of the syringe barrel defines a wide opening that receives a plunger in sliding, fluid-tight engagement with the walls of the syringe barrel. The distal end of the syringe barrel defines a narrow opening that permits a controlled fluid flow to or from the fluid receiving chamber in accordance with the direction of movement of the plunger. The distal end of the syringe barrel also is configured for receiving a needle cannula.

The prior art syringe must be packaged to ensure sterility until it is used. Some prior art syringes are sealed to protect their sterility in packages. These prior art syringes are accessed by opening the package shortly prior to use of the syringe. Other prior art syringes are considered self-contained in that the syringe barrel forms part of the sterile packaging. The typical prior art self-contained syringe includes a removable cap sealingly engaged over the proximal end of the syringe barrel to sterilely enclose both the wide entrance to the chamber and the plunger that is slidingly engaged in the chamber. The distal end of the prior art self-contained syringe also includes a removable cap-like shield that covers the needle cannula and sealingly engages the distal end of the syringe barrel. The caps of the prior art self-contained syringe are intended to define a barrier that bacteria cannot traverse. Thus the chamber, the plunger and the needle remain sterile until the syringe is used.

The prior art self-contained syringe is placed in condition for use by removing the proximal cap from the proximal end of the syringe barrel to expose the plunger and by removing the cap-like shield from the distal end of the syringe barrel to expose the needle cannula. The prior art self-contained syringe may then be filled with a selected dose of a drug, and the drug may be dispensed in a known manner. Self-contained hypodermic syringes of this type are commonly used by diabetic patients for self-administration of insulin.

Self-contained syringes offer many packaging conveniences and efficiencies with corresponding cost savings. However, prior art self-contained syringes do not provide the superior tamper evidence that is inherently provided by a separate hermetically sealed container for a syringe.

The cap-like needle shield of the above-described self-contained syringe often is discarded or misplaced immediately after the initial removal from the syringe barrel. Thus, if a sharps collector is not immediately available, the used hypodermic syringe may be left in an accessible location with the potentially contaminated needle fully exposed.

The prior art includes some hypodermic syringes with a syringe barrel and a tubular needle guard slidably mounted around the syringe barrel. The prior art tubular needle guard is releasably retained in a proximal position on the syringe barrel prior to use of the hypodermic syringe. In this pre-use condition, the needle cannula is protectively enclosed by a cap-like needle shield. Immediately prior to use, the cap-like needle shield is removed to expose needle cannula. The hypodermic syringe is then used with the tubular needle guard retained in its proximal position on the syringe barrel. After use of the hypodermic syringe, the tubular needle guard is slid distally along the syringe barrel and is locked into a position where the tubular needle guard protectively surrounds the used needle cannula. The prior art includes several different structures for releasably retaining the tubular needle guard in its proximal position and for locking the needle guard in its distal position. Hypodermic syringes of this general type are shown in U.S. Pat. Nos. 5,304,149; 5,342,309; 5,385,555; and 5,403,287.

SUMMARY OF THE INVENTION

The subject invention is directed to a self-contained syringe that is sterilely sealed prior to use, and that helps protect against accidental needle sticks after use.

The self-contained syringe of the subject invention includes an elongate tubular syringe barrel having a widely opened proximal end, a narrowly opened distal end and a fluid receiving chamber therebetween. A plunger is disposed in the fluid receiving chamber and is in sliding fluid-tight engagement with the tubular walls of the syringe barrel that define the chamber. A plunger rod projects proximally from the plunger and is accessible from the open proximal end of the syringe barrel. A sterile cap releasably engages the proximal end of the syringe barrel and covers the plunger to help ensure sterility for the fluid receiving chamber.

A needle cannula is mounted to the distal end of the syringe barrel, such that the lumen through the needle cannula communicates with the fluid receiving chamber. The needle cannula may be permanently mounted to the distal end of the syringe barrel or releasably mounted thereto by, for example, a luer connector.

The self-contained syringe of the subject invention further includes a substantially rigid tubular safety shield mounted around the syringe barrel for sliding telescopic movement relative thereto. The self-contained syringe is initially disposed in an as-packaged condition with the safety shield being releasably held in an intermediate position on the syringe barrel and protectively surrounding the needle cannula. This initial releasable connection of the safety shield to the syringe barrel may be achieved with a frangible heat stake or ultrasonic weld that can be selectively broken by manual force as explained further herein. Alternatively, a controlled application of a frangible or releasable adhesive may be used to releasably secure the safety shield at the intermediate position on the syringe barrel and in surrounding relationship to the needle cannula. Separation of these frangible or releasable connections provides tamper evidence. As a further embodiment, interengageable structures on the safety shield and the syringe barrel may be employed to achieve this releasable connection.

The safety shield may be moved proximally from the intermediate as-packaged position on the syringe barrel into a proximal as-used position where the needle cannula is exposed for use. This movement between the intermediate and proximal positions may be achieved by breaking the heat stake, ultrasonic weld, adhesive or other frangible or releasable connection or by disengaging the interlocked structures.

After use of the hypodermic syringe, the safety shield may be moved distally to an after-use position relative to the syringe barrel. The safety shield and the syringe barrel preferably include locking means for permanently locking the safety shield and the syringe barrel in the after-use position to prevent a re-exposure of the used needle cannula.

The permanent locking of the safety shield in the distal after-use position may be achieved by locking structure near the proximal end of the safety shield and corresponding locking structure near the distal end of the syringe barrel. The locking structure may include a restraining ring mounted to the syringe barrel and/or to the safety shield. Locking may be achieved by a simple linear movement of the safety shield relative to the syringe barrel, for example, as described in U.S. Pat. Nos. 5,342,309 and 5,385,555. Alternatively, the locking structure may require a combination of linear and rotational movement to achieve the permanent locking of the safety shield in the distal after-use position, for example, as described in U.S. Pat. No. 5,403,287.

The self-contained syringe further includes a shield for preventing contamination of the needle cannula and the chamber of the syringe barrel prior to use. The sterile shield may comprise a cover positioned across the distal end of the rigid tubular safety shield. The cover may include a peel-off tab that can be removed immediately prior to moving the rigid tubular safety shield from the as-packaged intermediate position to the as used proximal position. Alternatively, the sterile cover may be a puncturable membrane that is punctured by the needle cannula as the rigid tubular safety shield is moved proximally from the intermediate as-packaged position to the proximal as-used position. Still further, the sterile cover may define a cap releasably engaged with the distal end of the rigid tubular safety shield.

BRIEF DESCRIPTION OF THE DRAWINGS

FIG. 2 is a cross-sectional view taken along line 2—2 in FIG. 1.

FIG. 3 is a cross-sectional view of an alternate safety shield and a removable cap FIG. 4 is a cross-sectional view similar to FIG. 2, but with the shield in the as-used position.

FIG. 5 is a cross-sectional view similar to FIGS. 2 and 4, but with the safety shield in the after-use position.

DETAILED DESCRIPTION OF THE PREFERRED EMBODIMENTS

Figure 1:
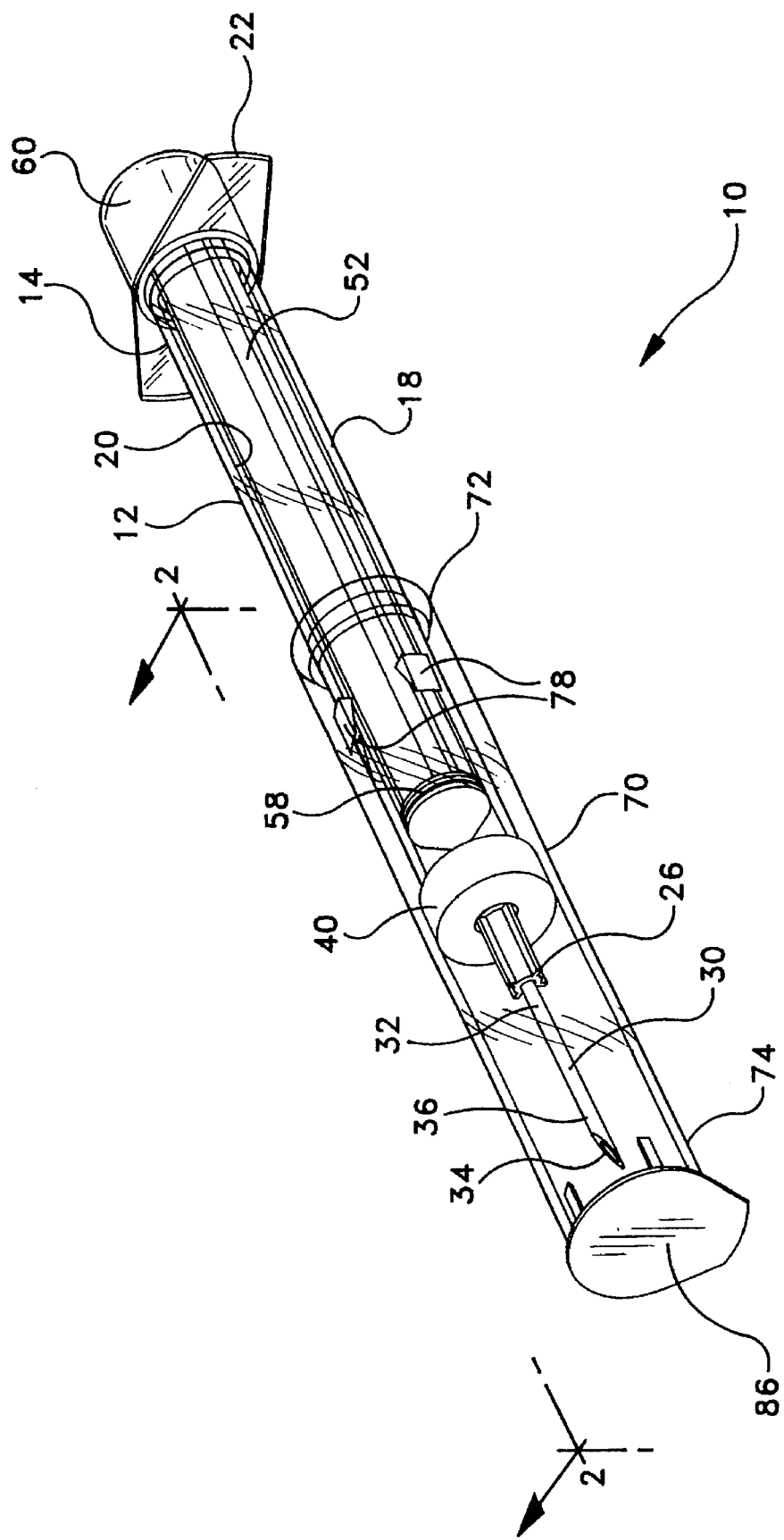
FIG. 1 is a perspective view of a self-contained syringe in accordance with the subject invention and in an as-packaged shielded condition.

Adverting to FIGS. 1–5, a self-contained syringe in accordance with the subject invention is identified generally by the numeral 10. Syringe 10 includes a syringe barrel 12 having a open proximal end 14, a distal end 16 and a cylindrical side wall 18 of outside diameter "a" extending therebetween. Side wall 18 defines a fluid receiving chamber 20 within syringe barrel 12. Proximal end 14 of syringe barrel 12 preferably includes a transverse flange 22 projecting outwardly therefrom to facilitate digital manipulation of syringe 10. A short cylindrical collar 24 preferably projects proximally from transverse flange 22 and surrounds the opening to fluid receiving chamber 20 of syringe barrel 12.

Distal end 16 of syringe barrel 12 includes an elongate tip 26 having a fluid passageway 28 extending axially therethrough and into communication with fluid receiving chamber 20 of syringe barrel 12.

Self-contained syringe 10 further includes a needle cannula 30 having a proximal end 32, a sharp distal tip 34 and a lumen 36 extending axially therebetween. Proximal end 32 of needle cannula 30 is securely affixed to tip 26 such that lumen 36 is in fluid communication with passageway 28 and with fluid receiving chamber 20 of syringe barrel 12.

A retaining ring 40 with an axial length "b" is rigidly locked into tight gripping engagement with the distal end of syringe barrel 12. Retaining ring 40 has a diameter "c" which exceeds the diameter "a" of syringe barrel 12. Thus, retaining ring 40 projects radially outwardly beyond tubular side wall 18 of syringe barrel 12. It is within the purview of the present invention to include a locking ring which is integrally formed with the syringe barrel to produce a one-piece structure which eliminates the need to assemble the retaining ring to the barrel. Also, it is within the purview of the present invention to include syringe barrel without a retaining ring, as will be discussed in more detail hereinafter.

Syringe 10 further includes a plunger assembly 50 having a plunger rod 52 with a proximal end 54 disposed externally of chamber 20 of syringe barrel 12 and a distal end 56 disposed within chamber 20. Plunger assembly 50 further includes an elastomeric stopper 58 securely mounted to distal end 56 of plunger rod 52. Stopper 58 is in sliding fluid-tight engagement with tubular wall 18 of syringe barrel 12 and functions to urge fluid into or out of portions of chamber 20 distally of stopper 58.

Self-contained syringe 10 further includes a proximal sealing cap 60 having a cylindrical side wall 62 with opposed proximal and distal ends 64 and 66. An end wall 68 extends continuously and unitarily across proximal end 64 of side wall 62. Distal end 66 of side wall 62 is releasably engaged with cylindrical collar 24 of syringe barrel 12 to seal chamber 20 and plunger assembly 50 from bacteria. Sealing cap 60 may also contain an air permeable material capable of filtering out bacteria, if desired. Sealing cap 60 may also contain structure allowing the passage of air but not bacteria, such as a labyrinth seal which is known in the art.

Syringe 10 further includes a cylindrical safety shield 70 having opposed proximal and distal ends 72 and 74. Proximal end 72 preferably includes an inwardly extending flange 76 having a diameter "d" that is equal or slightly greater than diameter "a" of syringe barrel 12 but less than diameter "c" of retaining ring 40. Thus, flange 76 is in close sliding engagement with the outer circumferential surface of cylindrical wall 18 of syringe barrel 12 at a location between retaining ring 40 and transverse flange 22, and is prevented from moving axially beyond these constraints. Safety shield 70 also is characterized by at least one and preferably a plurality of locks 78 between flange 76 and distal end 74 of safety shield 70. Each lock 78 includes a proximally facing locking surface 80 and a distally and inwardly facing ramp surface 82. Distance "e" between locking surface 80 and flange 76 is slightly greater than axial length "b" of retaining ring 40.

Distal end 74 of shield 70 includes inwardly directed projections 84 which are dimensioned to releasably engage retaining ring 40 for releasably holding shield 70 in a proximal as-used position on syringe barrel 12. A peel-off tab 86 is heat sealed across distal end 74 of safety shield 70. Tab 86 may contain or be made of an air permeable material capable of filtering out bacteria. Tab 86 may also be made of material which is not air permeable. The sterilization process and other design factors will determine the choice of tab material. The tab material may also be made of easily pierceable material so that the syringe assembly may be used without removing the tab, as will be explained in more detail hereinafter. FIG. 3 shows a distal cap 186 as an alternate to peel-off tab 86. Distal cap 186 includes an end wall 188 and a cylindrical side wall 190 that resiliently engages distal end 74 of shield 70 sufficiently tight to define a bacterial barrier. Distal cap 186 can be disengaged by exerting distally directed forces on tab 192. Distal cap 186 may also contain an air permeable bacterial filter material or other structure to allow air to pass therethrough but not bacteria. Such structures are known in the art.

In the as-packaged condition shown in FIGS. 1 and 2, distal end 74 of safety shield 70 projects distally beyond needle cannula 30. Thus, safety shield 70 protects against accidental contact with needle cannula 30. Safety shield 70 is preferably held in this as-packaged condition of FIGS. 1 and 2 by frangible heat stake connections 88 to retaining ring 40. The frangible heat stake connections 88 can be broken by exerting proximally directed, distally directed and/or rotational forces on safety shield 70 relative to syringe barrel 12 by, preferably, gripping the shield as shown by the hand illustrated in FIG. 2. The absence of the frangible heat stake connection provides temper evidence. Cylindrical safety shield 70 may also be connected to retaining ring 40 through the use of adhesives or interlocking mechanical structures such as an annular groove around the circumference of the retaining ring and a corresponding annular flange around the inside diameter of the safety shield.

The combination of annular flange 76 slidingly engaged with tubular wall 18 of syringe barrel 12 and peel-off tab 86 (FIGS. 1 and 2) or distal cap 186 (FIG. 3) across distal end 74 of safety shield 70 provides a bacterial barrier for needle cannula 30 and portions of chamber 20 distally of stopper 58. Thus, these structures in combination with proximal cap 60 provide bacterial protection for all of chamber 20, plunger assembly 50 and needle cannula 30. Accordingly, the preferred self-contained syringe of the present invention needs no further packaging to maintain its sterility before use. The syringe assembly acts as its own package. It is within the purview of the present invention to include a self-contained syringe without a retaining ring. For example, a self-contained structure can be achieved by attaching inwardly directed flange 76 directly to the syringe barrel at a position where the safety shield is held in the as-packaged position of FIG. 4.

Self-contained syringe 10 is placed in the as-used condition of FIG. 4 by removing peel-off tab 86 or distal cap 186, unless the distal end of the safety shield is covered by a pierceable barrier material, and exerting a proximal force on safety shield 70 relative to syringe barrel 12. The proximal force on safety shield 70 will sever frangible heat stake connections 88, or other connection as taught hereinabove, and permit safety shield 70 to slide proximally along syringe barrel 12 until needle cannula 30 is sufficiently exposed for use. Proximal cap 60 may then be removed and syringe 10 is used in the conventional manner by slidably moving plunger assembly 50 relative to syringe barrel 12 for drawing a selected drug into chamber 20 and subsequently injecting the drug through needle cannula 30.

After use, needle cannula 30 is protectively and permanently shielded by advancing cylindrical shield 70 distally relative to syringe barrel 12. Sufficient distal movement of shield 70 urges ramped surfaces 82 of locks 78 into retaining ring 40. Ramping forces generated by surfaces 82 cause a resilient local expansion and deflection of shield 70 sufficient for locks 78 to pass distally beyond retaining ring 40. After sufficient distal movement, shield 70 will resiliently return toward an undeflected condition such that retaining ring 40 is captured between radial surfaces 80 of locks 78 and flange 76 on shield 70 as shown in FIG. 5. This locking engagement prevents further movement of shield 70 in either a distal direction or a proximal direction. Hence, sharply pointed distal tip 34 of used needle cannula 30 is protectively shielded from accidental contact.

As a further alternative, movement of shield 70 from the as-packaged condition in FIG. 2 to the as-used condition of FIG. 4 can include structure which requires relative rotation between shield 70 and syringe barrel 12 for aligning grooves and ribs on the opposed surfaces. Prior to such alignment, axial movement between shield 70 and syringe barrel 12 is prevented. However, after such rotation, axial movement is permitted until shield 70 is locked into the after-use position shown in FIG. 5 above. These and other variations will be apparent to persons skilled in the art after having read applicant's disclosure.

What is claimed is:

1. A self-contained syringe comprising:

a syringe barrel having a side wall with an open proximal end, a distal end and a fluid receiving chamber therebetween;

a needle cannula projecting from said distal end of said syringe barrel and communicating with said fluid receiving chamber;

a plunger slidably mounted in said open proximal end of said syringe barrel;

a proximal seal releasably engaging said proximal end of said syringe barrel; and a tubular safety shield having a distal end with a distal seal and an opposed proximal end slidable disposed on said syringe barrel, said safety shield and said barrel including means for releasably retaining said shield at an intermediate position on said syringe barrel such that said safety shield protectively encloses said needle cannula, said safety shield being movable sequentially to a proximal position where said needle cannula is exposed for use and subsequently to a distal position where said safety shield is locked in surrounding relationship to said needle cannula.

2. The syringe of claim 1, wherein said means for retaining said shield in said intermediate position on said barrel includes a frangible adhesive connection between said syringe barrel and said safety shield for releasably engaging said safety shield in said intermediate position on said syringe barrel.

3. The syringe of claim 2, wherein said frangible connection includes frangible heat-stake connection between said syringe barrel and said safety shield.

4. The syringe of claim 2, wherein said frangible connection includes a frangible sonic weld connection between said syringe barrel and said safety shield for releasably engaging said safety shield in said intermediate position on said syringe barrel.

5. The syringe of claim 1, wherein said distal seal comprises a peel-off tab attached to said distal end of said safety shield and forming a sterility barrier to protect said needle cannula from contamination.

6. The syringe of claim 1, wherein said distal seal comprises a cap releasably engaged with said distal end of said safety shield and forming a barrier to protect said needle cannula from contamination.

7. The syringe of claim 1, wherein said syringe barrel further includes a retaining ring at said distal end, said safety shield including locking structure for lockingly engaging said retaining ring when said shield is in said distal position on said syringe barrel.

8. The syringe of claim 7, wherein said locking structure includes an inwardly extending flange on said proximal end of said safety shield, said flange being dimensioned for preventing slidable advancement of said safety shield distally beyond said retaining ring.

9. The syringe of claim 8, further comprising a plurality of inwardly directed locks on said safety shield between said flange and said distal end of said safety shield, said locks being disposed to lockingly engage said retaining ring between said locks and said flange of said safety shield.

10. The syringe of claim 9, wherein said locks are angularly inclined for facilitating local deflection of said safety shield as said safety shield is moved into said distal position on said syringe barrel.

11. The syringe of claim 7, wherein said distal end of said safety shield is dimensioned for releasable frictional engagement with said retaining ring when said safety shield is in said proximal position on said syringe barrel.

12. A self-contained syringe comprising:

a syringe barrel having a side wall with an open proximal end, a distal end and a fluid receiving chamber therebetween;

a tubular safety shield having opposed proximal and distal, said safety shield being telescoped over said syringe barrel and being slidably movable between a proximal position where said distal end of said syringe barrel is exposed and a distal position where said distal end of said syringe barrel is shielded;

a proximal seal 60 releasably and sterilely engaged over said proximal end of said syringe barrel;

a distal seal releasably and sterilely engaged over said distal end of said safety shield; and a frangible tamper-evident means seal holding said safety shield at an intermediate position on said syringe barrel with said distal end of said safety shield and said distal seal enclosing said distal end of said syringe barrel, whereby removal of said distal seal and breaking of said frangible connection permits said safety shield to be moved sequentially to said proximal position for use of said syringe and to said distal position for shielding of said syringe.

13. The syringe of claim 12, further comprising locking means on said safety shield and said syringe barrel for locking said safety shield in said distal position.

14. The syringe of claim 12, wherein said syringe barrel further includes a needle cannula projecting at said distal end and communicating with said fluid receiving chamber, said safety shield surrounding said needle cannula in said intermediate position and in said distal position.

15. The syringe of claim 12, further comprising a plunger slidably mounted in said open proximal end of said syringe barrel, said proximal seal releasably and sterilely enclosing said plunger.

16. The syringe of claim 12, further comprising means for releasably holding said safety shield in said proximal position on said syringe barrel.

* * * * *